United States Patent [19]

Cantor et al.

[11] Patent Number: 4,613,459
[45] Date of Patent: Sep. 23, 1986

[54] LYMPHOCYTE GROWTH FACTOR

[75] Inventors: Harvey I. Cantor, Boston; Gary Nabel, Cambridge, both of Mass.

[73] Assignee: Dana-Farber Cancer Institute, Boston, Mass.

[21] Appl. No.: 435,510

[22] Filed: Oct. 20, 1982

[51] Int. Cl.$^4$ .......................... C07K 3/28; C12N 5/00; C12N 5/02; C12N 1/38
[52] U.S. Cl. ................................... 530/351; 435/240; 435/241; 435/244
[58] Field of Search ....................... 260/112 R, 112 B; 424/177, 101, 85; 435/240, 241, 244; 514/2, 21

[56] References Cited

U.S. PATENT DOCUMENTS

| | | | |
|---|---|---|---|
| 4,172,124 | 10/1979 | Koprowski et al. | 424/85 |
| 4,271,145 | 6/1981 | Wands et al. | 128/763 |
| 4,323,561 | 4/1982 | Nowotny | 424/180 |
| 4,333,562 | 6/1982 | Kim | 424/195 |
| 4,438,032 | 3/1984 | Golde et al. | 260/112 R |

OTHER PUBLICATIONS

Watson, (1979) "Continuous Proliferation of Murine Antigen-Specific Helper T-lymphocytes in Culture" *J. Exp. Med.* 150, 1510-1519.
Wagner et al., *J. Exp. Med.* 148: 1523 (1978) "T-T-Cell Interactions During in Vitro Cytotoxic Allograft Responses."
Yamauchi et al., *Eur. J. Imm.* 11:905 (1981) "Analysis of Antigen-Specific, Ig-Restricted Cell-Free Material Made by I-J+Ly-1 Cells (Ly-1-Tsi F) . . . ".
Nabel et al., *Cell* 23:19 (1981) "Use of Cloned Populations of Mouse Lymphocytes to Analyze Cellular Differentiation."
Nabel et al., *Proc. Natl. Acad. Sci.* USA 78:1157 (1981) "T-Cell-Dependent Activation of Resting B-Cells Requirement for Both Non-Specific Unrestricted and Antigen-Specific Ia-Restricted Soluble Factors."
Watson et al., *J. Exp. Med.* 150:849 (1979).
Andersson et al., *Proc. Natl. Acad. Sci.* USA 781:2497 (1981).
Takatu et al., *Immunol.* 125:2646 (1980).
McDougal et al., *J. Exp. Med.* 145:693 (1977).
Altman and Katz, *Adv. Immunol.* 33:73-166 (1982).
Kohler and Milstein, *Nature* 256:495 (1975).
Lee et al., *Clinical Immunology Newsletter* 1:1 (Sep. 1980).
Weis, Adres et al., *Cellular Immunology*, Ch. 34, (1977).
Strickberger, *Genetics* (McMillan, 1976) pp. 610 et seq.
Cerrotini et al., *J. Exp. Med.* 140:703. (1974), "Generation of Cytotoxic T Lymphocytes in vitro".
Hayflick, *Tissue Culture, Methods and Applications*, ed. Krire et al., (New York: Academic Press, 1973).
Quintans and Lefkowits, *Eur. J. Immunol.* 3:392 (1973).
Laemli, *Nature* 227:680 (1970).
Laskey et al., *Eur. J. Biochem.* 56:335 (1975).
Nabel, *Nature*, 291:332 (1981).

*Primary Examiner*—John Kight
*Assistant Examiner*—Nathan M. Nutter
*Attorney, Agent, or Firm*—David G. Conlin; Ernest V. Linek

[57] ABSTRACT

A family of growth factors, methods of making and using such growth factors in in vivo treatment of living mammalian cells, and products incorporating such growth factors, are disclosed.

The growth factors were isolated from the supernatant fluid obtained by incubation of inducer T-cells in the presence of a suitable antigen or mitogen. The growth factors disclosed include a 14 Kd polypeptide which stimulates growth of both T-cells and B-cells, a 50 Kd polypeptide which stimulates B-cells to multiply and secrete immunoglobulins, and a 45 Kd growth factor which stimulates secretion of immunoglobulins by B-cells and stimulates rapid growth of certain mast cells, stem cells and certain other types of cells.

13 Claims, 5 Drawing Figures

4,613,459

LYMPHOCYTE GROWTH FACTOR

BACKGROUND OF THE INVENTION

This invention relates to products for stimulating growth of mammalian cells and methods for making and using such products. In its preferred embodiments, the invention pertains to growth factors for treating ailments of the immune system and other systems of mammals by stimulation of growth of mammalian cells, particularly T-cell lymphocytes, B-cell lymphocytes, mast cells, stem cells, fibroblasts, etc., in order to enhance or restore physiological functions provided by those cells, e.g., to enhance or restore the effectiveness of the immune system to resistance of disease.

The immune system in mammals depends substantially on the development and proliferation of T and B-cell lymphocytes for humoral and cell mediated immune response. Mammals often suffer from immunodeficiencies, which may be congenital, such as genetically caused failures to manifest efficient humoral and/or cellular responses to infections. Some immuno deficiencies may be acquired, e.g. those associated with malnutrition, radiation, aging, malignancy or debilitation.

Most immune responses are initiated by proteins produced by a set of T lymphocytes called inducer cells. These cells synthesize and secrete peptides that stimulate growth and differentiation of many cell types, including lymphocytes and monocytes that kill foreign organisms, see Wigner et al., *J. Exp. Med.* 148: 1523 (1978), Yamauch et al., *Eur. J. Imm.* 11:905 (1981), as well as B lymphocytes, Nabel, et al. *Cell* 23:19, (1981), mast cells, Nabel, *Nature* 291: 332 (1981) and hematopoietic precursor cells, Nabel et al, *Proc. Natl. Acad. Sci.* U.S.A. 78:1157 (1981), the disclosure of these references being incorporated herein by reference. The biologic activities of these inducer molecules are not totally understood in molecular terms.

One approach in attempting to overcome immunodeficiencies has been to attempt to develop products for administration which will foster rapid growth of lymphocytes in order to enhance immune response and prevent disease. See e.g. U.S. Pat. No. 4,323,561 to Nowotny, and U.S. Pat. No. 4,333,562 to Kim, the disclosures of which are incorporated herein by reference.

For example, Watson, et al., *J. Exp. Med.* 150:849 (1979) and others have reported the obtaining of a factor from inducer molecules which Watson called Interleukin-2 (IL-2) and which Watson, et al., also called "T-Cell Growth Factor," because of its effect on T-cell growth. See Andersoon, et al., *Proc. Natl. Acad. Sci. U.S.A.* 78:2497 (1981); Takatu et al., Immunol. 125:2646 (1980); McDougall et al., *J. Exp. Med.* 145:693 (1977), the disclosures of which are incorporated herein by reference. However, there has been a great deal of confusion and conflicting reports of properties and size of molecules IL-2 and the many other factors of lymphokines produced by different T-cells, T-cells hybridomas, etc., in response to different conditions or stimulating agents. See Altman and D. H. Katz, "The Biology of Monoclonal Lymphokines Secreted by T Cell Lines and Hyhbridomas," *Adv. Immunol.* 33: 73–166 (1982), the disclosure of which is incorporated herein by reference.

SUMMARY OF THE INVENTION

The present invention relates to a family of growth factors having various properties, to methods of making and using such growth factors in in vivo treatment of living mammalian cells, and to products incorporating the growth factors.

The growth factors of the present invention were originally isolated from the supernatant fluid obtained by incubation of inducer T cells in the presence of a suitable antigen, e.g., sheep red blood cells, (SRBC) or mitogen, e.g. concanavalin A. The growth factors include a 14 Kd polypeptide which stimulates growth of both T cell and B cell lymphocytes and many other types of cells; a 50 Kd polypeptide which stimulates B cells to multiply and secrete immunoglobulins and a 45 Kd growth factor which stimulates secretion of immunoglobulins by B cell lymphocytes, and stimulates rapid growth of certain mast cells, stem sells and certain other cells.

DETAILED DESCRIPTION OF THE INVENTION

Figure 1:
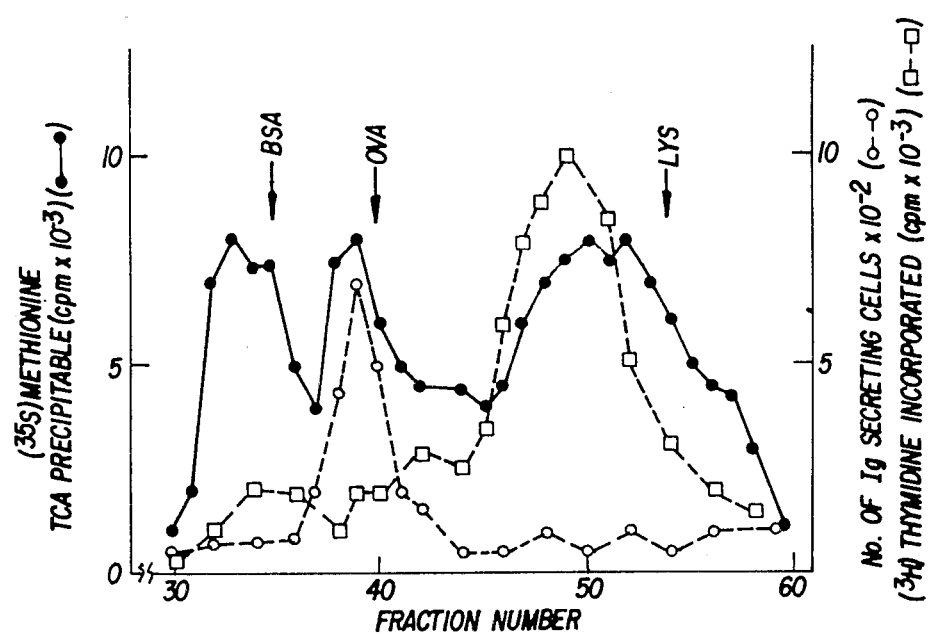
FIG. 1 is a graph showing the various proteins separated on a Sephadex G100 column by elution of the supernatant fluid derived from stimulated incubation of cloned inducer T cells, along with the effect of various fractions in (a) inducing immunoglobulin secretion from B cells and (b) inducing T-cell proliferation, as measured by incorporation of tritiated thymidine.

A primary object of the present invention stems from the discovery of a protein, which acts as a growth factor for both T lymphocytes and B lymphocytes, and methods for making and using the protein. More specifically, we have produced and isolated a polypeptide having a molecular weight of approximately 14 kilodaltons (Kd) which stimulates proliferation of both T and B cells, as well as other cell types, including mast cells, fibroblasts, and stem cells. This 14 Kd peptide is believed to be normally associated with different larger peptides which may serve to focus its mitogenic activity to one or another target cell. The polypeptide which is a prime subject of this invention shows a molecular weight of 14 Kd as established by sodium dodecyl sulfate SDS polyacrylamide gel electrophoresis, and confirmed by Sephadex G-100 column chromatography. The polypeptide has an isoelectric point (pI) of about 4.0 as established by flat bed isoelectric focusing. The 14 Kd lymphocyte growth factor is a potent agent, with significant growth being induced with as little as a fraction of a nanogram per millimeter of that polypeptide. Thus, this polypeptide is active at concentrations similar to those observed for peptide hormones. The rate of T or B cell proliferation induced by the 14 Kd polypeptide is virtually identical to the rates achieved by use of the lymphocyte mitogens, such as concanavalin A for T cells, or lipopolysaccharide (LPS) for B cell proliferation. However, unlike LPS, the 14 Kd polypeptide does not induce B cells to secrete immunoglobulins.

A further problem with mitigens like LPS is that they apparently only affect growth of a cell once, and after an initial stimulation to proliferation, the cells become resistant to further stimulation. This is not the case with the growth factors of the present invention.

The 14 Kd lymphocyte growth factors of the present invention can be obtained and isolated in a number of ways. For example, the protein can be isolated from supernatant peptides synthesized by stimulated inducer T cells, preferably cloned T-cells. Thus, an inducer T cell clone Cl. Ly1+2−/9, produced as described by Nabel et al., *Cell* 23:19 (1981) a sample of which has been deposited with the American Type Culture Collection, Rockville, Md., under the accession number ATCC CRL-8179, can be stimulated by incubation with an appropriate antigen or mitogen, such as sheep red blood cells (SRBC) or concanavalin A. The supernatant fluid from the thus stimulated inducer cells contains several proteins, from which the 14 Kd lymphocyte growth factor can be isolated, e.g. by gel electrophoresis or by chromatographic or other separation methods. Preferably, the proteins are separated by a combination of techniques, which may include chromatography, e.g. on a column of Sephadex (Pharmacia Fine Chemicals), DEAE cellulose, or other hydrophyllic resins which give effective separation of proteins in the molecular weight range of the proteins, high pressure liquid chromatography (HPLC), isoelectric focusing, and/or SDS polyacrylamide gel electrophoresis.

The 14 Kd lymphocyte growth factor may also be obtained from certain other polypeptides by treatment with dissociating agents, such as urea or SDS, or by treatment under conditions which favor protein dissociation, such as incubation in the absence of a carrier protein.

For example, supernatant fluid resulting from the incubation of inducer T cells, e.g., clone Cl. Ly1+2−/9 separated by chromotography on Sephadex G-100 resin, which does not favor protein dissociation, results in separation of polypeptides having a molecular weight of approximately 30 Kd and approximately 45–50 Kd. The 30 Kd fraction induces growth of T cells, but does not induce growth of B cells. The 50 Kd fraction has the properties of stimulating B-cells to divide, and also stimulating B-cells to secrete immunoglobulins, but the 50 Kd fraction had no effect on T cell growth. This 50 Kd polypeptide is considered to be another newly discovered growth factor, active for B-cell proliferation and Ig stimulation in a manner similar to the B-cell mitogen, lipopolysaccharide (LPS).

These larger molecular weight polypeptides can be separated into smaller protein segments by treatment with dissociating agents and or under dissociating conditions. Preferably, the larger proteins are treated with concentrated urea (1–10M, preferably 5–7M) or 0.01–1% (preferably about 0.08–0.2%) SDS, or other detergent. Other dissociating agents or chaotropic agents are known in the art. Reducing agents, such as dithiothreital (DTT), may not be effective. Alternately, the protein may simply be incubated at elevated temperatures, e.g. 30°–45° C., preferably 35°–40° C., in the absence of a carrier protein. Where treatment with dissociating agents or at elevated temperatures adversely effects the molecules, dissociation can be accomplished by less stringent techniques, e.g., by isoelectric focusing.

Treatment of the 30 Kd protein with a dissociating agent does not significantly alter its ability to induce T cell proliferation, but at least partially dissociated it into the 14 Kd lymphocyte growth promoter of the present invention and another fragment of about 16 Kd in molecular weight. Because of the presence of the 14 Kd polypeptide in the 30 Kd dissociation product, that product stimulates proliferation of B-cells, at a rate approximately equal to the rate produced by the known B-cell mitogen LPS.

The 50 Kd protein, treated with a dissociating agent such as SDS, results in a dissociation product with enhanced mitogenic activity for B-cells, and that dissociation product, unlike the 50 Kd protein itself, has the ability to stimulate growth of T-cells. However, the 50 Kd polypeptide loses the ability to stimulate B-cells to produce immunoglobulin when the dissociation is brought about by treatment by SDS, or by incubation at 37° C. for four hours in the absence of a protein carrier.

Dissociation of the 50 Kd protein without loss of the ability to stimulate B-cell secretion of immunoglobulins can be accomplished by flat bed isoelectric focusing. Subjecting the 50 Kd protein to isoelectric focusing produces two products: (a) a 45 Kd (SDS-PAGE) protein having an isoelectric point of about 6.0 which simulates B-cells to produce immunoglobulins and (b) the 14 Kd protein (pI about 4.0) described above, which has growth promoter activity for T-cells, B-cells and other cells, as indicated above. The 45 Kd protein constitutes another aspect of the present invention, for, while it does not cause growth of T-cell or B-cell lymphocytes, it is useful to stimulate B-cell lymphocytes to produce immunoglobulins. Moreover, the 45 Kd protein has been found to induce growth of mast cells, which are important sources of heparin, histamines, prostaglandins, and other physiologically important materials. The same 45 Kd protein also induces stem cells to give rise to new monocytes and granulocytes, which aid in prevention of infection. This protein has been used in vivo to stimulate maturation of stem cells in mice. Thus mammals who have had white blood cell production curtailed for various reasons may be treated with this growth factor to stimulate stem cells to mature more quickly, and thus rapidly decrease the mammal's susceptibility to infections.

The growth factors of the present invention can be utilized in vitro to grow a wide variety of cells in culture which are presently very difficult to maintain in a viable state. Thus the growth factors can be added to the culture medium to help maintain and/or grow mammalian cell lines based on cells which are responsive to the growth factors, e.g., cells from human or other mammal immune systems, nervous systems, epidermal systems, or other cell lines which are otherwise difficult to maintain. Addition of these growth factors is particularly effective in maintaining cell lines of lymphocytes, mast cells, fibroblasts, stem cells, etc. Additional of about 0.1 ng/ml to about 1 mg/ml, preferably about 1 ng/ml to about 10 ng/ml to a culture broth containing the appropriate nutrients, and other standard or optional ingredients, results in substantial improvements in cell line viability. In many cases, the use of the growth factors of the present invention can obviate the need to use feeder cells, such as irradiated cells, in order to maintain a cell line. This has substantial advantages, e.g.

from the standpoint of purity of products of the cell line.

The lymphocyte growth factors of the present invention may be used in vivo to treat immuno-deficiencies resulting from genetic or acquired causes, including congenital failure to manifest efficient humoral (B cell antibody) response and/or cellular (T cell) response to infestations, as well as immuno-deficiencies caused by toxic drug reactions, infections, radiation, malnutrition, malignancy, etc., in man or other mammals.

The growth factors can be administered individually, or in combination. For example, the 45 Kd growth factor has a growth-stimulating effect on mast and other cells, but not on B cell lymphocytes. The effect of the 45 Kd factor on B-cells is to stimulate secretion of immunoglobulins by the B-cells. If it is desired to stimulate both mast cell growth and B-cell growth and immunoglobulin secretion, either the 50 Kd growth factor, or mixture of the 45 Kd factor and the 14 Kd factor may be administered.

For enhancing growth of particular target cells in the animal, the present growth factors can advantageously be convalently or otherwise bound or associated with an agent which binds to or otherwise becomes associated with the target tissue. Thus, for example, the 14 Kd growth factor, which has a growth stimulating effect on many types of cells, may be made more specific in its effect in the subject animal by attaching it to an antibody for a target cell, e.g., the animal's lymphocytes. One way to effectively accomplish this specificity is by raising monoclonal antibodies to the animal's target tissue, coupling the 14 Kd growth factor to the monoclonal antibody, and infusing the coupled antibody/growth factor into the animal's blood stream. The antibody carries the growth factor to the target tissue, the antibody attaches or otherwise associates with the target tissue and the growth factor stimulates proliferation (and/or secretion) by that target tissue.

The techniques for obtaining antibodies to specific antigen are generally known, per se, and a number of monoclonal antibodies are available as commercial products, e.g., from New England Nuclear Corp., Boston, Mass. The techniques for making monoclonal antibodies were first described by Kohler and Milstein, *Nature* 256:495 (1975), the disclosure of which is incorporated herein by reference. Various aspects and variations of this technique have been reported. See, e.g., I. Lu, et al., *Clinical Immunology Newsletter* 1:1 (Sept, 1980), (and references cited therein) U.S. Pat. No. 4,172,124, to Koprowski et al., U.S. Pat. No. 4,211,145, to Wands, et al., the disclosures of which are incorporated herein by reference. If preferred, this antibody can be raised against target cells from the individual animal who is to be treated. For example, T-cell or B-cell lymphocytes can be obtained from an individual animal or human, innoculated into a source of antibodies, e.g., a mouse, rabbit, another animal of the same species as that to be treated, or with a culture of cells which produce antibodies, e.g., a culture of B-lymphocyte cells or B-cell precursor cells, obtained from a desired mammal, whereby antibodies, preferably monoclonal antibodies, to the target cells as produced, and the antibody producing cells can be maintained by forming hybridomas or by appropriate cloning and culturing techniques. The growth factors of the present invention can be used to advantage, both in maintaining the growth of the cells, and in inducing secretions of antibodies.

The antibodies to target cells can be coupled together with the growth factor proteins of the present invention by use of any multifunctional reagent which reacts with proteins without denaturing or otherwise adversely affecting the physiological properties of the antibody or of the growth factor. Preferably, the coupling agent is a bifunctional agent of relatively low molecular weight which reacts with reactive groups on the protein molecules.

A number of such reagents are known in the art, including metaxylyline diisocyanate, toluene 2,4 diisocyanate, p,p'diflouro-m'm-dinitrodyphenyl sulfone, toluene-2-isocyanate-4-isothiocyanate, 3-methoxydiphenylmethane-4,4'diisocyonate, benzidine diisocyanate, 1,5-naphthalenedisulfonyl chloride and 3,6-bis-(acetatomercurimethyl)dioxane, and others. See, e.g. D. M. Weis, G. A. Andres, et al., "Immunologic Techniques for the Identification of Antigens or Antibodies by Electro Microscopy", *Cellular Immunology*, Ch. 34 (1977), the disclosure of which is incorporated herein by reference. Presently preferred is metoxylyline diisocyanate.

Preferably, both reagents should be comparatively pure. Unwanted antibodies should be removed from the desired antibody, e.g., by absorbtion of appropriate antigen or by other known techniques, e.g., chromatography on DEAE cellulose or other suitable material. The higher the purity of the antibody, the better the yield of the conjugated antisera/growth factor. Other purification steps for the antisera to be used may include precipitation in sodium sulfate, and/or chromatography, e.g., on DEAE cellulose.

The antibody is conjugated to the growth factor, first by coupling the multifunctional coupling agent to one or the other of the antibody or the growth factors, and then by coupling the remaining substituent to a remaining reactive site on the coupling agent. For example, where metaxylyline diisocyanate is used as the coupling agent, the 14 Kd, 45 Kd or 50 Kd growth factor (GF) may be reacted with metaxzylylene diisocyanate to form the mono-ureido substituted compound in accordance with equation (1), followed by reaction of the mono-ureido substituted compound with antibody Ab for the target cells in accordance with equation (2).

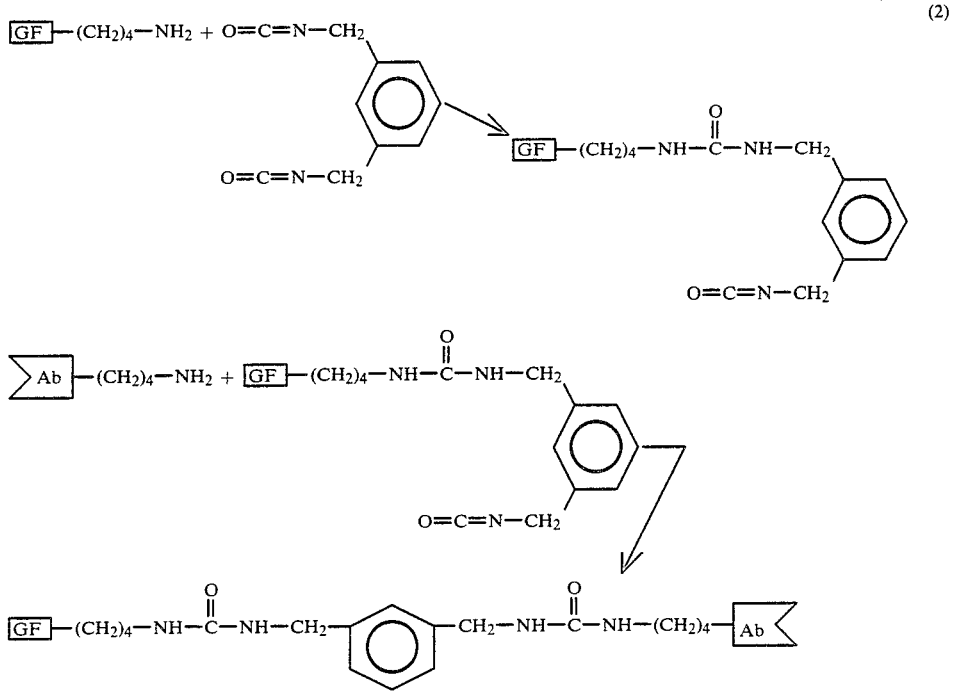

(2)

See Andres, et al., supra, at 34.2–34.4. As pointed out by Andres, et al., the reaction product can be tested to confirm the completeness of the reaction and the continued specificity of the conjugated antibody for the target cells.

Throughout this application, where molecular weights in kilodaltons have been referred to, the apparent size of the molecules is meant. This apparent molecular size in kilodaltons corresponds to the molecular weight of the proteins although, as is known in the art, variations in apparent molecular size, may be observed for the same protein or other biological material, depending on the type of test utilized, the conditions under which the test is run, the degree of glycosylation of the protein, conformational considerations, variations in chromatographic or electrophoretic media, and for other reasons. While the variety of methods reported here indicated a relatively small amount of variation in parameters such as apparent molecular weight, other tests, chromatographic media, conditions, etc., may give somewhat different results. It is the growth, and Ig secretion inducing proteins themselves which are important to the present invention, and the intent and scope of the invention cannot be avoided by making, using, or selling such proteins produced or tested by using conditions or methods under which the apparent molecular weight or other parameters vary from the figures reported here. As is known in the art, the amino acid sequence of these proteins can be determined. See, e.g., Strickberger, Genetics at 610 et seq. (McMillan, 1976), the disclosure of which is incorporated herein by reference. Devices for automatically sequencing proteins are available from Beckman Instruments, Co., and Applied Biosystems, Inc.

The amount required of the various growth factors to be used in in vivo treatment (hereinafter referred to as the active ingredient) varies with the route of administration and with the nature and severity of the condition to be treated, and ultimately is at the discretion of the physician or veterinarian. In general, however, for each of these utilities the dosage will be in the range of about 1 ng. to 1 Mg. per kilogram body-weight of mammal, and preferably about 10 to 200 mg/kg. All dosages calculated with reference to the peptide base.

The active ingredients may be administered by any route appropriate to the condition to be treated, suitable routes including oral, nasal (e.g., by spray) and parenteral (including subcutaneous, intramuscular and intravenous). It will be appreciated that the preferred route will vary with the condition to be treated.

While it is possible for the active ingredient to be administered as the raw chemical, it is preferable to present it as a pharmaceutical formulation preparation. The formulations of the present invention, both for veterinary and for human use, comprise an active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof. Desirably the formulation should not include oxidizing agents and other substances with which peptides are known to be incompatible. The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; or as a solution or a suspension in an aqueous liquid or a non-aqueous liquid; or as an oil-in-water liquid emulsion or a water-in-oil liquid emulsion. The active ingredient may also be presented as a bolus, nasal spray, electuary or paste.

A tablet may be made by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding, in a suitable machine, a mixture of the powdered compound moistened with an inert liquid diluent.

Formulations suitable for parenteral administration conveniently comprise sterile aqueous solutions of the active ingredient which solutions are preferably isotonic with the blood of the recipient. Such formulations may be conveniently prepared by dissolving solid active ingredient in water to produce an aqueous solution, and rendering said solution sterile may be presented in unit or multi-dose containers, for example sealed ampoules or vials.

It should be understood that in addition to the aforementioned ingredients the formulations of this invention may include one or more additional ingredients such as diluents, buffers, flavouring agents, binders, surface active agents, thickeners, lubricants, preservatives (including anti-oxidants) and the like.

Where the formulation, for human or for veterinary use, is presented in unit dosage form, for example those unit dosage forms specifically mentioned above, each unit thereof conveniently contains the active ingredient (as above defined) in an amount in the range of about 100 ug to about 100 mg. The invention will be further illustrated by the following illustrative embodiments.

EXAMPLES

Generation of Cl. Ly1+2−/9 Cells

Cells for cloning were obtained from C57B1/6TL+ mice (available from E. A. Boyse). Cells from BALB/c mice were used to produce conditioned medium. The BALB/c mice were obtained from Jackson Laboratory.

The procedure used for initiating cell lines was that disclosed in Nabel et al., *Cell* 23:19 (1981), which is incorporated herein by reference.

The conditioned media used in cloning and maintaining cells was prepared as follows: Dulbecco's modified Eagles Media (DME) (GIBCo), was further modified by supplementation with arginine and asparagine in accordance with the method of Cerrotini, et al., *J. Exp. Med.* 140:703 (1974), the disclosure of which is incorporated herein by reference, and 0.006 g/l of folic acid, sodium pyruvate and essential vitamins. This media is hereinafter referred to as "modified" DME or MDME.

BALB/c spleen cells ($5 \times 10$ ml) were incubated at 37° C. for 45 hours in 40 ml of MDME which had been further supplemented with $5 \times 10^{-5}$M 2-mercaptoethanol (2-ME), 2 mM additional glutamine, 4% heat-inactivated fetal calf serum (FCS) and 2 mg/ml of Con A (Calbiochem-Behring Corp.) in tissue culture flasks (Falcon Plastics 30240) having an atmosphere containing 10% $CO_2$. Supernatant from this culture was filtered through an 0.20 m Nalgene filter, and designated as conditioned medium (CM).

Cells were grown in "complete conditioned medium" (CCM), made by combining 50% CM and 50% MDME, and further supplementing with $5 \times 10^{-5}$M 2-ME, 2 mM fresh glutamine, and sufficient additional FCS such that the final concentration of FCS was 10% of the total volume. Cell concentrations were maintained between 0.5 and $3 \times 10^5$ cells/ml, and cultures supplemented with fresh CCM (approximately 1:4) every other day. Cell cultures were maintained in the absence of antibiotics and checked periodically for mycoplasma contamination in accordance with Halblick, "Screening Cultures for Mycoplasma Infections," Krire, et al (Ed.) *Tissue Culture, Methods and Applications* (Academic Press, N.Y. 1973), the disclosure of which is incorporated herein by reference.

The following cloning procedure was used. Cells were distributed into microwells (Falcon plastic microtiter plates 3040) at estimated final concentrations of 100, 10, 1 and 1, cells/well. Each well contained 0.1 ml of CCM and irradiated (1500 rad) cell monolayers from different tissues (final concentrations 4 to $8 \times 10^5$ cells/well). Cultures were supplemented every two days with 30-ul CCM until colonies were visible (10 days to 3 weeks) in wells that initially received less than 100 cells/well.

Cloning efficiency (CE) was calculated according to Poisson distribution (Quintans and Lefkowits, *Eur. J. Immunol.* 3:392 (1973) (incorporated by reference)). At least 96 wells were used to calculated each CE. The fraction of negative wells was plotted as a function of the logarithm of initial cell number. Single cells from colonies arising at frequencies of $<36\%$ with CE$>5\%$, regrown twice starting either after dilution at 3 cells/10 wells or after single cell micromanipulation, were termed clones. The characteristics of the initial cell colonies were stable and identical to those of cloned populations derived from them by single cell micromanipulation or redilution; separate tests of more than 12 different cell colonies showed that three to ten daughter clones, derived from each, expressed identical cell-surface antigens, morphology and, when relevant, the function of the parent colony.

After cloning, cells were grown in the absence of irradiated cell monolayers. They were maintained at concentrations of 0.5 to $3 \times 10^5$ cells/ml in CCM. Cloned cells were initially transferred to 2 ml wells (Linbro plates, Flow Labs) fed with 0.5 ml CCM, and maintained at 0.5 to $3 \times 10^5$/ml. Cells were maintained at this concentration in Linbro plates, Petri dishes (Falcon 1007, 1008, 3003) or tissue culture flasks (Falcon 3024) depending on cell volume. Cells that adhered slightly to plastic tissue culture flasks were grown in Petri dishes to facilitate recovery. Doubling times ranged from 18–48 hr for all cells tested. Cells could be expanded to numbers $>10^8$.

The phenotype of the various clones can be determined by incubation with appropriate antibodies, followed by conjugation with fluorescein and analysis using flow cytofluorometry. Phenotype can also be checked by incubation with lymphoid cells, e.g. cells from B6 mice which express the relevant cell surface antigen, or cells from a congeneric inbred "partner" strain that differs only at the locus coding for the relevant cell-surface antigen. See Nabel et al., supra, Volume 23 of *Cell* at page 25. Monoclonal antibodies, e.g. those specified for Thy 1.2, Lyt 1.2 and Lyt 2.2 are commercially available, e.g. from New England Nuclear Corp., and the procedures per se are known in the art.

One of the clones Cl. Ly1+2−/9 is a cloned population of T cells expressing the Thy1+Lyt1+2− "inducer" T cell phenotype. This clone has been grown in CCM at concentrations of 0.5 to $3 \times 10^5$/ml in continuous culture for more than 15 months.

Preparation of B Lymphocytes

To obtain B lymphocytes, C57Bl/6 mouse (Jackson Laboratories) spleen cell suspensions were incubated on rabbit anti-mouse Ig coated plates. After discarding the non-adherent cells, Ig+ cells were eluted by vigorous pipetting. The eluted cells were incubated with monoclonal anti-Ly 1.2, anti-Ly 2.2 and anti-Thy 1.2 at optimal lytic conditions for 35 min at 4° C., washed and incubated an additional 30 min at 37° C. with rabbit compliment. Lack of residual T cells was verified by immunofluorescence with monoclonal anti-Thy 1.2 antibody as well as by the absence of anti-SRBC plaque forming cell responses after in vitro stimulation by SRBC.

Biological Assays of T Cell Function

The ability of various growth factors from the stimulated supernatants of cloned T cell populations to stimulate immunoglobulin secretion by B cells "in vitro" was determined by adding such factors to $1-10 \times 10^{-5}$ B cells from non-immune donors in a final volume of 0.2 ml. These cell cultures were stimulated with $10^6$ SRBC for 5 days before anti-SBRC PFC or total PFC (total number of Ig secreting plaque forming cells) were enumerated by a modification of the hemolytic plaque assay described by Nabel et al, supra, 23 Cell at 26. Horse erythrocytes (25 ul) were counted with rabbit anti-mouse F(ab')2 and 25 ul of the cell culture to be tested were mixed in $12 \times 25$ mm test tubes with 450 ul of a 0.8% solution of Sea-Plaque agarose (Maine Colloids) in a special balanced salt solution (SBSS). The contents of each tube were immediately layered on 2 ml of gelled 1% Sea Kem agarose (Maine Colloids) in a $30 \times 10$ mm Petri dish. After 1 hr at 37° in a humid atmosphere containing 5% $CO_2$, 0.35 ml of rabbit anti-mouse F(ab')2 developing serum (final dilution 0.05 mg/ml in SBSS) was pipetted onto the Petri dishes. After another hour at 37° C. the antiserum was decanted and replaced with an equal volume of reconstituted guinea pig complement (Grand Island Biological Co.) diluted 1:10. Zones of lysis (plaques) were enumerated 2 hr later. In all cases erthryocyte PFC and total PFC were determined from triplicate cultures.

T cell proliferation was determined using a cloned Thy1+Ly1−2+ population cloned as described above, whose growth is completely dependent upon IL-2. B cell proliferation was determined using highly purified resting B cells (obtained as described above). $1-3 \times 10^4$ cloned T cells or $2-10 \times 10^4$ B cells were incubated in flat bottom microtiter wells in 0.2 ml Delbecco's modified Eagles medium, 4% heat inactivated FCS, 50 uM 2-ME and 2 mM glutamine with various fractions of supernatants or mitogens. After 20-68 hr. of incubation, 0.5 uCi of 3 H-thymidine was added to each well. Four hours later, the radioactivity incorporated by the cells was measured by retention on glass fiber filters.

Internal Labelling of Supernatant Proteins

Radiolabelled supernatant material from cloned cells was generated in serum-free conditions as follows: cells from the continuously growing clone were incubated with SRBC ($10^6$) or concanavalin A (2 u/ml) for 6 hours, washed three times, and incubated at a cell concentration of $10^6$/ml in methionine-free RPMI 1640 medium (Roswell Park Memorial Institute) that was supplemented with 2 mM glutamine, 5 ug/ml human transferrin, 5 ug/ml bovine insulin, 20 U/ml aprotinin and 100 uCi/ml $^{35}$S-methionine. After 4 hr at 37° C. unlabelled methionine was added to bring the final methionine concentration to 1 mM. Cells were centrifuged and 0.1 mg/ml ovalbumin added to the supernatant as a carrier protein before centrifugation at high speed ($100,000 \times g$) prior to use.

Purification of Growth Factors

All procedures were done at 0°-4° C. After centrifugation, $^{35}$S-methionine labelled supernatant from $50 \times 10^6$ cloned Cl. Ly1+2−/9 cells was concentrated 10 to 20 fold and dialyzed against phosphate buffered saline (PBS) containing 5% glycerol, 100 mM KCl and 0.5 mM phenylmethylsulfonylfluoride (PMSF). Concentrated supernatant material was applied to a Sephadex G-100 column ($100 \times 2$ cm) equilibrated with the same buffer. 2 ml fractions were collected and aliquots of each fraction were tested for (1) TCA precipitable radioactivity, and (2) biological activity, namely (a) Stimulation of Ig secretion by purified B cells, and (b) Stimulation of T cells to divide as measured by ability to incorporate tritiated thymidine. The column was equilibrated with the following standards: bovine serum albumin BSA, (68,000 Kd) ovalbumin (OVA), (45,000 Kd) and lysozyme (LYS), (13,000 Kd)

The results are depicted in FIG. 1. As is evident from that Figure, one radiolabelled protein, having a molecular weight of approximately 45-50 Kd, was active in inducing Ig secretion from B-cells, but not active in inducing growth of T-cells. Another protein, having a molecular weight of approximately 60-66 Kd, did not have either biological activity. The third protein, eluted as an broad molecular weight band of 12-30 Kd, actively induced T-cell proliferation, but did not induce secretion of Ig by B-cells.

Polyacrylamide Gel Electrophoresis

Electrophoresis was carried out in 0.7 mm thick slab gels using a modification of the method of Loemli, Nature 227:680 (1970). Supernatant aliquots (25 ul), internally labeled as described above, were mixed with an equal volume of 160 mM Tris-HCl (pH 6.8) 20% glycerol, 4% SDS, 0.2% Bromophenol Blue and 200 mM dithiothreitol. Gels containing 12.5% acrylamide were electrophoresed at 120 V constant voltage. The gels were stained with Coomassie Blue and subjected to the fluorographic treatment in accordance with the method of Laskey et al., Eur. J. Biochem 56:335 (1975), dried and autoradiographed.

Figure 2:
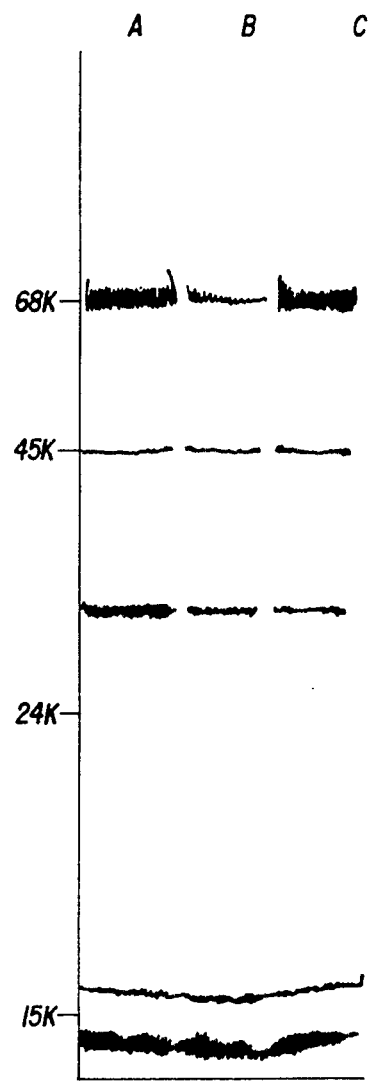
FIG. 2 is a copy of an SDS-PAGE electrophoretogram, Showing the components of various fluids, as further described below.

FIG. 2 presents the results for three different Cl. Ly1+2−/9 supernatant fluids: (a) the supernatant from Cl. Ly1+2−/9 which has been stimulated by incubation with SRBC, (b) supernatant from Cl. Ly1+2−/9 which has not been stimulated, i.e., it has been incubated in the absence of antigen or a mitogen, and (c) supernatant from Cl. Ly1+2−/9 which was stimulated by incubation with concanavalin A. As shown in FIG. 2, SDS polyacrylamide gel electrophoresis of supernatant peptides synthesized by unstimulated inducer cells showed 5 major labelled protein bands (apparent m.w. of 60, 45, 33, 30, and 16 Kd) as well as several minor bands. In the presence of correct antigen (SRBC) or concanavalin A, the cells synthesized a new polypeptide of an apparent mol. wt. of 14 Kd. No other internally labelled proteins showed an obvious or reproducible change in intensity after stimulation by antigen or mitogen.

Growth Induction From Stimulated and Unstimulated Supernatants

The amount of increased growth rate of T-cells and B-cells induced by exposure to supernatant proteins from stimulated and unstimulated Cl. Ly1+2−/9 cells was determined by measuring the rate of uptake of tritiated thymidine by the T or B cells. Further, stimulated and unstimulated B cells were exposed to SRBC, and the amounts of anti-SRBC immunoglobulin secreted by the B-cells was assayed.

Supernatant from Cl. Ly1+2−/9 cells was prepared by incubating $10^6$ cells/ml for 4 hrs in RPMI 1640 medium supplemented with 5 ug/ml transferrin and 5 ug/ml insulin immediately after the cells had been incubated for six hours (and washed twice) either without stimulant, or with stimulation by 2 ug/ml of Con A, $10^6$ cells/ml of SRBC or $10^6$ cells/ml of chicken erythrocytes (CRBC) (which is the wrong antigen for anti-SRBC secretion). Supernatants were tested for induction of T or B cell proliferation by $5 \times 10^4$ cells and induction of anti-SRBC secretion by $5 \times 10^5$ purified B cells.

TABLE I

INDUCTION OF FUNCTION AND PROLIFERATION IN Cl.Ly1+2−/9 SUPERNATANT BY CON A OR ANTIGEN

| Induction of Cl./ Ly1+2−/9 | ($^3$H) Thymidine Incorporation | | Anti SRBC PFC/$10^6$ |
|---|---|---|---|
| | T-cells | B-cells | B-cells |
| none | 485 ± 125 | 3,751 ± 543 | 0 |
| Con A | 17,543 ± 528 | 21,878 ± 528 | 2,397 ± 110 |
| SRBC | 13,353 ± 381 | 20,777 ± 1,543 | 310 ± 18 |
| CRBC | 487 ± 395 | n.d. | 98 ± 35 |
| Positive Control: | | | |
| (LPS 4 mcg/μl) | 362 ± 110 | 130,987 ± 2,345 | 4,230 ± 134 |
| (Con A (2 μgs/ml) | 6,146 ± 82 | 2,984 ± 640 | 0 |

Mitogenic Activity of Purified 14 Kd Polypeptide

The activities of the 14 Kd peptide and others were tested in a similar manner after separation on preparative SDS polyacrylamide gels. One millimeter slices were cut from the slab gel in the region corresponding to 10 to 20 Kd. Proteins in each slice were extracted and tested for TCA preciptable radioactivity and function. As expected, only the slices corresponding to 14 Kd and 16 Kd bands had extractable protein (measured by TCA-precipitable radioactivity). After extensive dialysis to remove SDS, the peptides were tested, at a level of 2 ng/ml for stimulation of T or B cell proliferation. Con A and LPS were used at 2 and 4 ng/ml for controls. The results are given in Table II.

TABLE II

ACTIVITIES OF SDS-PAGE PURIFIED PEPTIDES

| Peptide added to cell culture (2 ng/ml) | ($^3$H) thymidine uptake (cpm) | | B-cell Ig secretion (PFC/$10^6$) |
|---|---|---|---|
| | T-cells | B-cells | |
| none | 187 ± 12 | 7,631 + 365 | 3 ± 1 |
| 14 Kd | 25,273 ± 432 | 93,387 ± 4,321 | 0 |
| 16 Kd | 289 ± 23 | 6,723 ± 1,323 | 0 |
| 14 Kd & 16 Kd | 20,104 ± 1,234 | 82,343 ± 6,001 | 0 |
| Control | | | |
| Con A | 23,240 ± 2,331 | 7,851 ± 652 | 0 |
| LPS | 199 ± 55 | 130,759 ± 3,211 | 6,531 ± 456 |

Peptides extracted from the slice corresponding to the labelled 14 Kd band induced growth of both T and B cells. Peptides from the 16 Kd band induced minimal cell proliferation, and the remaining 10–20 Kd slices did not stimulate division. Protein from the 60 Kd band contained substantial TCA-precipitable radioactivity but did not stimulate division of either cell type. Mixtures of 14 Kd and 16 Kd peptides have approximately additive effects upon proliferation of T or B cells.

The purified 14 Kd peptide is a potent inducer of cell proliferation. As little as 1 ng/ml of the 14 Kd peptide induces lymphocyte growth even after extraction from SDS-containing gels and thus is active at concentrations similar to those observed for peptide hormones. At similar concentrations, the tempo of T or B cell proliferation induced by the 14 Kd peptides was virtually identical to stimulation of growth by the lymphocyte mitogens, concanavalin A and lipopolysaccharide (LPS). However, unlike LPS, no concentration of the 14 Kd peptide induced B-cell Ig secretion.

Determination of Terminal Amino Acid Sequence

A portion of 14 Kd polypeptide, obtained from 2d gel was treated with carboxypeptidase Y. The amino acids which were released were dialyzed and identified by two dimensional chromatography on polyamide sheets. The solvents for the two dimensional chromatography were formic acid (1.5%) followed by a 9:1 mixture of benzene/acetic acid. The amino acids obtained were alanine, phenylanine and glycine. It was concluded that this C-terminal portion of the 14 Kd polypeptide Gly-Phe-Ala.

Production of 14 Kd Polypeptide from Large Proteins

As noted, above, the 50 Kd polypeptide obtained by Sephadex G-100 chromatography in the example described above, is a new B-cell growth factor, not previously isolated or described. In addition, the factor corresponding to a molecular weight of about 30 Kd in Sephadex chromotography showed biologic activity, inducing T cells, but not B cells, to proliferate.

To determine whether these two active fractions bore any relationship to the 14 Kd growth factor, the 30 Kd and the 50 Kd fractions were treated with dissociating agents and/or under dissociating conditions. By "dissociating conditions" is meant conditions which are such as to favor separation of proteins into their major substituents without destroying the properties of those substituents.

Aliquots of Sephadex G-100 column fractions 38–40 (mean apparent MW 50 Kd) and 48–50 (mean apparent MW 30 Kd) (see FIG. 1), were treated either with 0.1% SDS, 6M urea, or 0.01M DTT (dithiothrietol) at room temperature for 30 minutes, or were incubated without carrier protein for 12 hours at 37° C. After incubation the samples were dialyzed and assayed for biologic activity. To minimize contaminant cells, $2 \times 10^4$ B cells were used for proliferation assays. As a control, the known mitogens Con A and LPS were employed for T cells and B cells respectively. 23,240 cpm were incorporated by T cells in the presence of Con A. LPS stimulated B cells absorbed 13,075 H-thymidine cpm, and formed 250 total PFC/$10^6$ cells and 165 SRBC PFC/$10^6$ cells. The results appear in Table III.

TABLE III

EFFECT OF DISSOCIATING AGENTS IN THE FUNCTIONAL ACTIVITY OF 30,000 AND 50,000 Mol. Wt. FRACTIONS FROM Cl.Ly1$^+$2$^-$/9 SUPERNATANT

| Fraction added: | ($^3$H) Thymidine Incorp. T cells | B cells | Anti SRBC PFC/$10^6$B cells | Total IG (PFC/$10^6$) |
|---|---|---|---|---|
| A. | | | | |
| 30 Kd | 18,740 | 963 | 0 | 65± |
| 30 Kd + SDS .1% | 14,750 | 7,833 | 0 | 40± |
| 30 Kd + Urea 6 M | 23,560 | 8,233 | 0 | 10± |
| 30 Kd + DTT 1 M | 9,870 | 1,531 | 0 | n.d. |
| 30 Kd + (4 hr × 37° C.) | 18,990 | 4,831 | 0 | n.d. |
| B. | | | | |
| 50 Kd | 1,110 | 3,531 | 890 ± 365 | 2,218 ± 610 |
| 50 Kd + SDS .1% | 16,540 | 7,005 | 54 ± 34 | 310 ± 414 |
| 50 Kd (4 hr × 37° C.) | 13,530 | 7,890 | 45 ± 56 | 262 ± 22 |

Treatment of the 30 Kd fraction with 6M urea or 0.1% SDS did not significantly alter its ability to induce T-cell proliferation; nor did incubation of this fraction at 37° C. for 12 hr in the absence of a carrier protein. However, all of these dissociation treatments resulted in acquisition of a new activity by the 30 Kd fraction: the dissociation products now stimulated vigorous proliferation of B cells, and this proliferation was equivalent to that induced by the B-cell mitogen LPS.

Similar treatment of the 50 Kd fraction gave analogous results. Although incubation at 37° C. for 4 hr, or with 0.1% SDS abrogated the ability of this fraction to induce B cells to secrete Ig, these treatments resulted in enhanced mitogenic activity for B cells and acquisition of mitogenic activity for T-cells.

Figure 3:
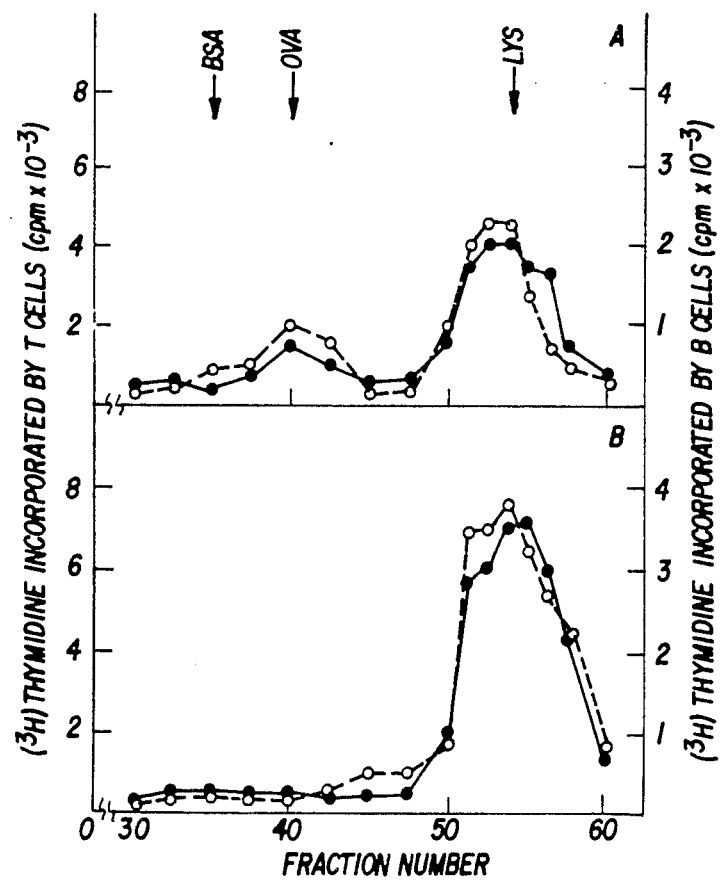
FIG. 3 depicts graphs of T-cell and B-cell proliferation after treatment with components of (A) the 50 Kd material and (B) the 30 Kd material.

In summary, the 30 and 50 Kd fractions acquired a common activity after treatment with SDS: they stimulated growth of both T and B cells. To determine the apparent MW of peptides responsible for this shared function following dissociation, the internally labelled 50 Kd and 30 Kd fractions were re-chromatographed. Both T and B cell growth activities now co-eluted at approximately 14 Kd as shown in FIG. 3. In that figure, curves relating to T cell proliferation are denoted by the solid circle, and curves relating to B cell growth are denoted by the open circles. Panel A shows the results for the SDS-treated 50 Kd fraction, and Panel B depicts the results for the SDS-treated 30 Kd fraction.

Flat-Bed Isoelectric Focusing

In order to further investigate the 50 Kd and 30 Kd materials, they were subjected to flat bed isoelectrofocusing.

This procedure was performed in a horizontal layer of Sephadex G-75 using an LKB system (LKB Instruments, Inc., Rockville, Md.). After dialysis (against distilled water) of active material eluted from DEAE-cellulose, 76 ml of material was added to a solution containing 4 ml of Ampholytes (pH 3.5–8) and 4 gm Ultrodex (both from LKB Instruments, Inc.) before application to a gel tray. The tray was transferred to cooling plates (10° C.) and subjected to electrophoresis for 16 h at 640 V constant voltage. After electrophoresis, the gel was sliced into 30 portions, the pH of each slice was measured, and each was passed through Sephadex G-25 columns ($9 \times 1$ cm) before protein was eluted with 4 ml phosphate-buffered saline (PBS) containing 0.02% ovalbumin as carrier.

Isoelectric focusing was particularly advantageous to dissociate the components of the 50 Kd protein, since the B-cell Ig secretion activity was destroyed when the protein was dissociated using SDS, but not so under isoelectric focusing. The results for this 50 Kd peptide are shown in FIG. 4.

Figure 4:
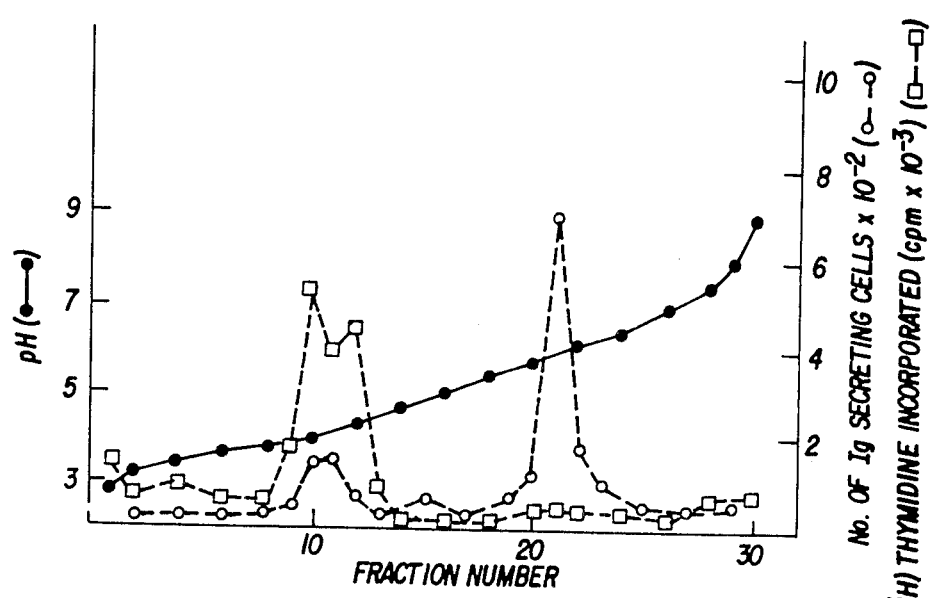
FIG. 4 depicts isoelectric focusing, immunoglobulin secretion and lymphocyte stimulation by isoelectrically disassociated components of the 50 Kd polypeptides.

As shown in FIG. 4, B-cell Ig secretion was induced by internally labeled peptides having a pI of approximately 6.0; T or B cell proliferation was induced by internally labelled peptides having a pI of approximately 4.0. The former internally labelled peptide (pI 6.0) resolved as a single band, MW 45 Kd, on SDS-PAGE, while almost all the latter peptide (pI 4.0) resolved as a single band of MW 14 Kd. Peptides having a molecular weight of 30 Kd after Sephadex fractionation were applied to SDS-PAGE slab gels. Repeated analysis of this material revealed two distinct bands, MW 14 Kd and 16 Kd, which contained approximately equal amounts of TCA precipitable cpm and acounted for >60–75% of the total cpm in the gel. The bands were eluted from the gel and tested for mitogenic activity. The 14 Kd peptide stimulated both T and B proliferation while neither the 16 Kd nor the fractions from 25 Kd–35 Kd had detectable mitogenic activity. The 30 Kd. fraction following Sephacryl chromatography was also separated by charge using isoelectrofocusing. Twenty-two different fractions were tested for mitogenic activity. Only a fraction having a pI of about 3.9–4.0 stimulated T and B cells. When the mitogenic fraction was subjected to SDS polyacrylamide gel electrophoresis, 85% of the cpm resolved at 14–16 Kd.

Figure 5:
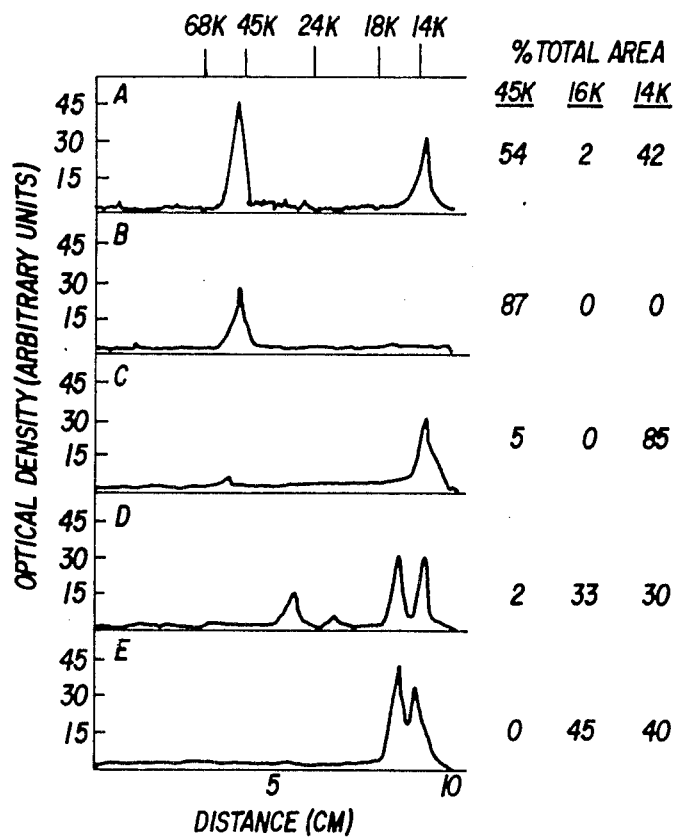
FIG. 5 is a set of graphs depicting the results of Optical Density Scanning of various fractions and materials.

FIG. 5 shows the results of densitometric scanning of SDS-PAGE from the following Cl. Ly1$^+$2$^-$/9 supernatant fractions: (A) The 50 Kd fraction after Sephadex G-100 chromatography; (B) The pI 6.0 fraction after separation of the 50 Kd material on IEF (see FIG. 4); (C) The pI 4.0 fraction from the 50 Kd material after separation on IEF; (D) The 30 Kd fraction after Sephadex G-100 chromatography; and (E) The mitogenic fractions (pI approximately 4.0) which were obtained after separation of the 30 Kd fraction on IEF.

Preparation of Growth Factors/Antibody Conjugates

As an example of the linking of growth factors to proteins which are specific to the target cells whose proliferation is desired, the 14 Kd growth factor can be conjugated to an antibody which binds to T-cells. The antibody used, for example, can be the monoclonal antibody Anti-human Ia (Clone 7.2), commercially available from New England Nuclear Corporation, which binds specifically to peripheral blood B-cells, so that more than 99% of the antibody binds to B-cells and less than one percent binds to peripheral blood T-cells or to cells in the thymus.

The coupling agent (metaxylylene diisocyanate) is first linked to the 14 Kd growth promoter protein. The purified protein is mixed in an ice bath with 0.05M phosphate buffer (ph 7.5) and 0.3M borate buffer (pH 9.5) in volume sufficient to give a final concentration of about 20 to 25 mg/ml of protein in 0.1M borate buffer. Cold liquid metaxylylene diisocyanate is added to the mixture at a ratio of 0.1 ml of metaxylylene diisocyanate per hundred mg of protein. The mixture is then stirred vigorously by magnetic stirrers on an ice bath for 45 minutes, and then is centrifuged at 4° and 1500 g for 30 minutes. The supernatant liquid contains the mono-substituted product, and is suitable for direct use in conjugation with the antibody.

Monoclonal Anti-human Ia (Clone 7.2, NEN), in phosphate buffered saline (pH 7.2) is admixed with this supernatant liquid prepared in the first step above, at a weight ratio of about 1 part of antibody to 4 parts of 14 Kd protein. Additional borate buffer is added to maintain about 0.1 and pH of about 9.5. The ingredients are stirred gently with a magnetic stirrer for 48 hours at 4° C.

Unconjugated antibody and/or protein can be removed by suitable techniques, e.g., electrophoresis, sucrose density gradient centrifugation, etc. As noted above, successful conjugation and continued specificity of the conjugated antibody can be confirmed by immunoelectrophoresis.

The resulting conjugate containing solution can be sterilized by passing through a bacterial filter (e.g., available from Millipore Corp.) and stored at low temperatures (4° C.) for extended periods of time before use.

Thus, the present invention includes a number of lymphocyte growth factors, one having a mean apparent molecular weight of approximately 14 Kd. and which has an isoelectric point of about 3.9-4, stimulates T cells and B cells and other types of cells to proliferate, but which does not itself stimulate Ig secretion by B cells. The 14 Kd growth factor can be produced by incubating inducer T cells in the presence of an antigen, and isolating the growth factor from the supernatant. It can also be produced by dissociation of larger peptides produced in such supernatant fluid when inducer T cells are incubated with or without the presence of an antigen or mitogen. More specifically, it can be produced from a protein found in such supernatant fluids having a mean apparent molecular weight of about 50 Kd which protein itself is a newly discovered growth factor for B cells. This B-cell growth factor can also be produced by separation from such stimulated supernatant fluids, e.g. by chromatographic, electrophoretic or isoelectrofocusing techniques. The 14 Kd growth factor can be produced by dissociating the 50 Kd B cell growth factor, or another protein from such supernatant fluid having a molecular weight of about 30 Kd, into their major parts. This can be accomplished, e.g., by treating the larger proteins with dissociating agents under dissociating conditions, or by isoelectrofocusing.

The products of the present invention can also be made by genetic engineering techniques, e.g., by at least partially analyzing the amino acid sequence of the desired material, using the amino acid sequence to obtain a DNA or RNA probe using the probe to determine the gene which makes the growth factor of interest, transforming that gene into, e.g., a suitable bacteria or yeast using an appropriate vector, replicating the gene and its bacterial host, and expressing the growth factor of interest. The resulting lymphocyte growth factors can be used to treat immunodeficiencies as above described.

The specific embodiments described herein are meant to be exemplary only, and various modifications will be apparent to those skilled in the art. The claims below are intended to cover all such modifications.

We claim:

1. A mammalian growth factor produced by
   (a) isolating mammalian inducer T lymphocytes having the characteristics of clone Cl. Ly1+2−/9,
   (b) stimulating growth factor production in said lymphocytes by contacting said inducer lymphocytes with an antigen or mitogen, and
   (c) isolating at least one growth factor from the material produced by the stimulated lymphocytes,
   said growth factor being selected from a growth factor for B- and T-cell lymphocytes having a molecular weight of about 14 kilodaltons, a growth factor for B-cell lymphocytes, and a growth factor for mast cells.

2. A mammalian growth factor according to claim 1 wherein said inducer T lymphocytes comprise cells of Clone Cl. Ly1+2−/9.

3. A mammalian growth factor according to claim 1 which stimulates the proliferation of B-cell lymphocytes, said growth factor having an apparent molecular weight of about 50 kilodaltons.

4. A mammalian growth factor according to claim 1 which stimulates mast cells, said growth factor having an apparent molecular weight of about 45 kilodaltons.

5. A mammalian cell growth factor according to claim 1, which is homogeneous.

6. A mammalian cell growth factor, comprising a polypeptide having a molecular weight of about 14 kilodaltons, which growth factor is functional to stimulate proliferation of both T and B cell lymphocytes.

7. The growth factor of claim 6, said growth factor also being functional to stimulate proliferation of mast cells and fibroblasts.

8. The growth factor of claim 6, wherein the growth factor has an isoelectric point of about 3.9 to 4.0.

9. A mammalian cell growth factor derived from mammalian inducer T lymphocytes having the characteristics of clone Cl. Ly1+2−/9, stimulated with an antigen or mitogen comprising a polypeptide having a molecular weight of about 50 kilodaltons, which growth factor is functional to stimulate proliferation of B cell lymphocytes.

10. The growth factor of claim 9, said growth factor also being functional to stimulate immunoglobulin secretion by B lymphocytes.

11. The lymphocyte growth factor of claim 9, wherein the growth factor has an isoelectric point of about 6.0.

12. A mammalian cell growth factor derived from mammalian inducer T lymphocytes, having the characteristics of clone Cl. Ly1+2−/9, stimulated with an antigen or mitogen, comprising a polypeptide having an apparent molecular weight of about 45 kilodaltons, which growth factor is functional to stimulate proliferation of mast cells.

13. The mammalian cell growth factor of claim 5, which growth factor is functional to stimulate the proliferation of mast cells.

* * * * *